United States Patent [19]

Kamiishi et al.

[11] Patent Number: 4,675,181

[45] Date of Patent: Jun. 23, 1987

[54] DEODORANT FOR PERMANENT WAVING AGENT

[75] Inventors: Yukio Kamiishi, Ohmiya; Hideo Ushioda; Takashi Akiyama, both of Tokyo, all of Japan

[73] Assignee: San-Ei Kagaku Co., Tokyo, Japan

[21] Appl. No.: 776,576

[22] Filed: Sep. 16, 1985

[51] Int. Cl.$^4$ ............................ A61K 7/09; A61K 7/11
[52] U.S. Cl. ........................................ 424/72; 424/71
[58] Field of Search .................................... 424/72, 71

[56] References Cited

U.S. PATENT DOCUMENTS

| | | |
|---|---|---|
| 4,235,898 | 11/1980 | Watanabe et al. ................ 424/70 |
| 4,345,080 | 8/1982 | Bolich, Jr. ........................ 424/70 |
| 4,366,099 | 12/1982 | Gaetani et al. .................... 424/64 |
| 4,379,753 | 4/1983 | Bolich, Jr. ........................ 424/70 |
| 4,416,868 | 11/1983 | Vanderberghe et al. ........... 424/70 |
| 4,430,250 | 2/1984 | Sebag et al. ...................... 424/72 |
| 4,612,188 | 9/1986 | Zorayan et al. ................... 424/72 |

FOREIGN PATENT DOCUMENTS 674195 6/1952 United Kingdom .

OTHER PUBLICATIONS

Sagarin, *Cosmetics Science & Technology*, pp. 520, 603-617 (1957).
Merck Index, 9th edition, Abst. #746, 4242, 4243, 742 (1976).

*Primary Examiner*—Leonard Schenkman
*Assistant Examiner*—F. Krosnick
*Attorney, Agent, or Firm*—Oldham, Oldham & Weber Co.

[57] ABSTRACT

According to the invention, a deodorant which comprises at least one of germanium, antimony and bismuth compounds is used for a permanent waving agent consisting mainly of a mercapto compound. The deodorant is utilized by being contained in the permanent waving agent, or applied as a pretreatment agent before the permanent waving operation is carried out.

By use of the above-mentioned deodorant, the production of hydrogen sulfide of "unpleasant odor" can be restrained.

12 Claims, 2 Drawing Figures

DEODORANT FOR PERMANENT WAVING AGENT

BACKGROUND OF THE INVENTION

1. Field of the Invention

The present invention relates to the removal of an unpleasant odor generated by use of a permanent waving agent containing a mercapto compound.

2. Description of the Prior Art

For a hair setting operation based on the permanent waving technique, hitherto, there have been widely carried out a method comprising reduction-breaking the disulfide bonds between the keratin molecules of hair by a reducing agent (usually called a primary agent such as thioglycolic acid and cysteine, and then oxidizing the broken parts by an oxidizing agent (usually called a secondary agent) such as bromate, perborate and hydrogen perxoride to form the disulfide bonds again.

When such a reducing agent as mentioned above, containing a mercapto compound, is used, however, it produces hydrogen sulfide having an unpleasant odor, with a defect giving an unpleasant feeling to these surroundings.

To cope with this problem, in general, a masking technique has been utilized whereby only the odor of a permanent waving agent can be weakened to some degree. But, it was next to impossible for the masking technique to inhibit the hydrogen sulfide odor generated through the reaction of a permanent waving agent with hair, this is an unpleasant odor.

To the purpose of obviating these defects, there have hitherto been proposed various kinds of counter-measures.

In British Pat. No. 674195, for example, a method for removing hydrogen sulfide produced by carrying out a permanent waving operation is disclosed, which comprises adding a tetrammine salt of zinc, copper, nickel or cobalt into a permanent waving agent consisting mainly of a thioglycollate.

This method is however not preferable, because these tetrammine salts, except for the zinc salt, form a colored chelate together with thioglycolic acid or the like and further oxidize thioglycolic acid.

In addition, the zinc salt must be used in a considerable amount to remove the unpleasant odor and has a defect of lowering the wave-forming power, this is an object of a parmanent waving agent, because it forms a strong complex together with thioglycolic acid.

Furthermore, there have been proposed various means, by way of example, as disclosed in Japanese Patent Publication No. 37013/1972, using an unsaturated carboxylic acid, Japanese Patent Publication No. 48740/1974 using honey and Japanese Patent Laid-Open No. 154116/1982 using a porous material and an air-tight cap, but it can not expect any satisfactory effect from all of these means.

SUMMARY OF THE INVENTION

After making various investigations for solving the above-mentioned defects of a permanent waving agent consisting mainly of a mercapto compound having a strong reducing power such as thioglycolic acid or cysteine, with keeping its merits, the inventors have found out that the unpleasant odor peculiar to a mercapto compound and the unpleasant odor of hydrogen sulfide produced in the operation of the permanent waving and its remaining odor can be easily removed by use of a small amount of a germanium, antimony or bismuth compound.

These compounds seldom to form a complex with a mercapto compound and do not lower the wave-forming power thereof, because its thiol group is not chelated.

Concerning the wave-keeping property, the feeling, the longterm stability of a chemical liquid and the test on the strength of hair, etc., the permanent waving agent in which the deodorant according to the invention is contained is not different from a conventional one.

It is an object of the present invention to provide a deodorant for a permanent waving agent consisting mainly of a mercapto compound, which comprises at least one of germanium, antimony and bismuth compounds.

One of the embodiments according to the invention is a deodorant such as the above-mentioned germanium compound or the like which is contained in a permanent waving agent consisting mainly of a mercapto compound, and another embodiment is a deodorant such as the above-mentioned germanium compound or the like which is used as a pretreatment agent for a permanent waving agent consisting mainly of a mercapto compound.

As the substances (called the deodorants) effective to remove an unpleasant odor which is generated when a permanent waving agent consisting mainly of a mercapto compound is used, according to the invention, one or more compounds are selected among the germanium, antimony and bismuth compounds. These compounds are preferably substances soluble in water, mercapto compounds and alkaline agents, and there can be concretely enumerated germanium dioxide, germanium tetrachloride, sodium metagermanate, antimony chloride, antimony sulfate, potassium antimonyl tartrate, bismuth nitrate, bismuth subnitrate, bismuth oxychloride and the likes.

By way of example, the mercapto compounds which are used as the reducing agent in a permanent waving agent consisting mainly of a mercapto compound, this is the object to be deodorized in the present invention, are thioglycolic acid, cysteine, thiolactic acid and their salts, or thioglycerine, glycerine monothioglycolic acid and the likes. The alkaline agents may be, for example, ammonia, monoethanolamine, diethanolamine, triethanolamine, isopropanolamine, ammonium bicarbonate, ammonium carbonate and the likes.

The ammonium odor resulted from the alkaline agents among these above-mentioned compounds will be masked by use of an odorivector such as perfume.

The first embodiment according to the present invention will be carried out in the mode of a deodorant such as a germanium compound which is contained in a permanent waving agent consisting mainly of a mercapto compound. As for the concentration of the deodorant, the above compound is preferably contained in an amount of about 0.01-5 wt % as a metal content, in particular at a rate of 0.05-2 wt %.

The second embodiment will be carried out in the mode of a deodorant such as a germanium compound which is used to treat hair as a pretreatment agent, for example in the form of an aqueous solution, before a permanent waving agent consisting mainly of a mercapto compound is applied in a usual manner to hair. In this case, the concentration of the deodorant will be utilized in the same range as limited in the first embodiment.

In general, a permanent waving agent is often used in the alkaline range in the viewpoint of its wave forming power, although it is usually used in the acidic to alkaline range.

The deodorant according to the present invention can produce a remarkable effect of restraining the production of hydrogen sulfide and further remove a remaining odor left after the operation of a permanent waving, in any mode of its application.

It is understood that in the present invention, the germanium compound or the like mentioned above reacts with generating hydrogen sulfide to produce a metal-sulfur compound, whereby the generation of an unpleasant odor is restrained.

Into a permanent waving agent, according to the present invention, there may be added useful substances which are usually added in a permanent waving agent, for example a pigment, perfume, penetrant, hair protective agent, hair tonic and the like.

In another mode of application, the deodorant according to the invention can be used by being applied on or impregnated in an end paper, cap or the like used in the permanent waving operation.

BRIEF DESCRIPTION OF THE DRAWINGS

Other objects, features and advantages of the prevent invention will be readily apparent from the following description of representative embodiments thereof, taken in conjunction with the accompanying drawings, although variations and modifications may be effected without departing from the spirit and scope of the novel concepts embodied in the disclosure, and in which.

DETAILED DESCRIPTION OF THE INVENTION AND PREFERRED EMBODIMENTS

The invention will be concretely described with reference to the test examples and embodiments mentioned below.

Test Example 1

Figure 1:
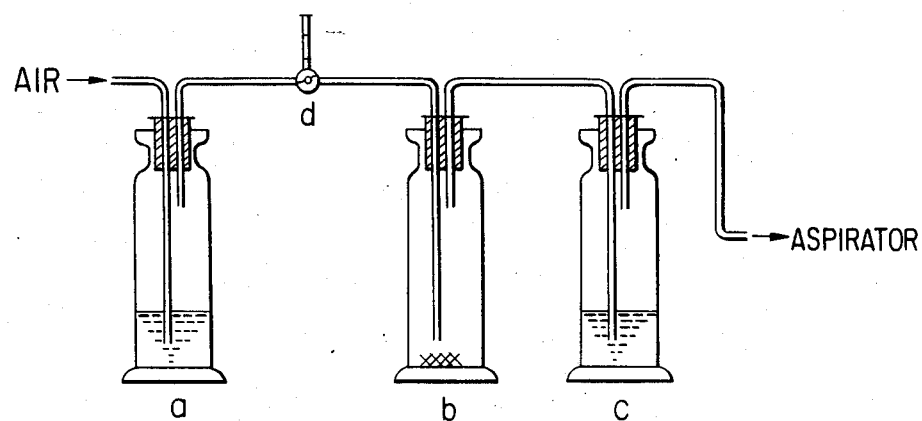
FIG. 1 is a schematic view showing a hydrogen sulfide sampling device.
Figure 2:
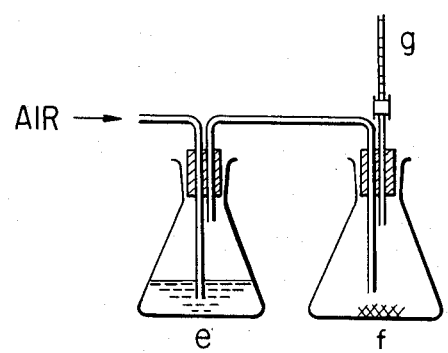
FIG. 2 is a schematic view showing a hydrogen sulfide determining device.

The test on the production of hydrogen sulfide which is produced from hair by its permanent waving treatment:

FIG. 1 of the accompanying drawings is a schematic view showing a hydrogen sulfide sampling device and FIG. 2 thereof is a schematic view showing a hydrogen sulfide determining device, wherein (a) is a 250 ml scrubbing bottle (100 m of liquid paraffin contained), (b): a 250 ml sample bottle, (c): a 250 ml absorption bottle (100 ml of an absorbing liquid contained), (d): an acid-pouring three-way cock, (e): a 200 ml scrubbing flask (100 ml of liquid paraffine contained), (f): a 200 ml sample flask, and (g): a detector tube.

The hydrogen sulfide sampling device shown in FIG. 1 was first used, 5 g of hair were charged in the sample bottle (b) in a constant temperature chamber kept at 25° C. and 50 ml of a conventional primary agent for permanent waving was added therein. After the hair was dipped thoroughly in the conventional primary agent and the sample bottle (b) was closed up, it was settled to continue the reaction for 15 minutes. Through the three-way cock (d), diluted sulfuric acid was added therein to regulate the pH of the liquid approximately at 2 to 2.5, and the absorption bottle (c) was continuously aspirated for 15 minutes.

The resulting absorbing liquid was analized in accordance with the JIS K0108 2(1) Volumetry (Iodimetric Titration) to determine the quantity of hydrogen sulfide.

$H_2S$ produced from 100 g of hair =

$$\frac{\text{(all the quantity of H}_2\text{S collected)} - \text{(blank test)}}{\text{(hair)}} \times 100$$

$$= \frac{2.98 \times 10^{-3} - 0.94 \times 10^{-3}}{5} \times 100$$

$$= 4.1 \times 10^{-2} \text{ g}$$

(Note) hair: prepared by washing untreated hair with a 0.5% aqueous solution of sodium lauryl sulfate, water-washing sufficiently and air-drying.

the quantity of $H_2S$ produced varied somewhat due to the property of sample hair.

EXAMPLE 1

The primary agent for permanent waving according to the invention, which contained the deodorant, and a conventional primary agent for permanent waving were used. The quantities of hydrogen sulfide, this is an unpleasant odor, produced when a permanent waving operation was carried out were detected and compared.

The apparatus used was the hydrogen sulfide determining device shown in FIG. 2.

Test Method: Hair was washed with a 0.5% aqueous solution of sodium lauryl sulfate. After washing with water thoroughly and air-drying, 1 g of hair was tied up in a bundle. In the constant temperature chamber kept at 25° C., a rod with the 1 g bundle of hair wound and fixed thereon was dipped in 20 ml of the primary agent for permanent waving according to the invention, prepared by the following prescriptions, and also in the same amount of the conventional primary agent for permanent waving, for 30 seconds, respectively. Immediately after extracting the liquid from these rods, each of the rods was charged in the sample flask (f) shown in FIG. 2 and it was closed up wherein the reaction was caused to continue for 15 minutes. The produced hydrogen sulfide was determined by use of the detector tube (g) in accordance with the JIS K0108 2(3) Detector Tube Method. The other examples mentioned were conducted through the same procedure.

| Prescription (wt %) | (1) | (2) | (3) | (4) |
|---|---|---|---|---|
| Ammonium thioglycollate (contained 50% as thioglycolic acid) | 12.0 | 12.0 | 12.0 | 12.0 |
| 28% Ammonia water | 3.0 | 3.0 | 3.0 | 3.0 |
| Germanium dioxide | 0.12 | — | — | — |
| Potassium antimonyl tartrate | — | 1.2 | — | — |
| Bismuth oxychloride | — | — | 0.75 | — |
| EMACAL VF (emulsifier made by San-Ei Kagaku Co. Ltd.) | 5.0 | 5.0 | 5.0 | 5.0 |
| Purified water | bal. | bal. | bal. | bal. |
| | 100 | 100 | 100 | 100 |

The pH value of these primary agents was 9.3. The concentration of each components is represented by weight percent based on all the volume of the primary agent. The results are shown in Table 1, wherein the numerical values mean ppm.

TABLE 1

| No. | Primary agents | Hydrogen sulfide produced |
|---|---|---|
| (1) | 0.12% of germanium dioxide contained (Ge: 0.08%) | 0 (ppm) |
| (2) | 1.2% of potassium antimonyl tartrate contained (Sb: 0.4%) | 0 |
| (3) | 0.75% of bismuth oxychloride contained (Bi: 0.6%) | 0 |
| (4) | Conventional | 190–200 |

EXAMPLE 2

| Prescription (wt %) | (5) | (6) | (7) | (8) |
|---|---|---|---|---|
| Ammonium thioglycollate (contained 50% as thioglycolic acid) | 12.0 | 12.0 | 12.0 | 12.0 |
| Monoethanolamine | 2.7 | 2.7 | 2.7 | 2.7 |
| Germanium dioxide | 0.12 | — | — | — |
| Potassium antimonyl tartrate | — | 1.2 | — | — |
| Bismuth oxychloride | — | — | 0.75 | — |
| EMACAL VF (above-mentioned) | 5.0 | 5.0 | 5.0 | 5.0 |
| Purified water | bal. | bal. | bal. | bal. |
| | 100 | 100 | 100 | 100 |

The pH value of these primary agents was 9.3. The concentration of each components is represented by weight percent based on all the volume of the primary agent. The results are shown in Table 2, wherein the numerical values mean ppm.

TABLE 2

| No. | Primary agents | Hydrogen sulfide produced |
|---|---|---|
| (5) | 0.12% of germanium dioxide contained (GE: 0.08%) | 0 (ppm) |
| (6) | 1.2% of potassium antimonyl tartrate contained (Sb: 0.4%) | 0 |
| (7) | 0.75% of bismuth oxychloride contained (Bi: 0.6%) | 0 |
| (8) | Conventional | 200–210 |

EXAMPLE 3

| Prescription (wt %) | (9) | (10) | (11) | (12) |
|---|---|---|---|---|
| Ammonium thioglycollate (contained 50% as thioglycolic acid) | 12.0 | 12.0 | 12.0 | 12.0 |
| Ammonium bicarbonate | 5.0 | 5.0 | 5.0 | 5.0 |
| Germanium dioxide | 0.12 | — | — | — |
| Potassium antimonyl tartrate | — | 1.6 | — | — |
| Bismuth oxychloride | — | — | 1.0 | — |
| EMACAL VF (above-mentioned) | 5.0 | 5.0 | 5.0 | 5.0 |
| Purified water | bal. | bal. | bal. | bal. |
| | 100 | 100 | 100 | 100 |

The pH value of these primary agents was about 7.6. The concentration of each components is represented by weight percent based on all the volume of the primary agent. The results are shown in Table 3, wherein the numerical values mean ppm.

TABLE 3

| No. | Primary agents | Hydrogen sulfide produced |
|---|---|---|
| (9) | 0.12% of germanium dioxide contained (Ge: 0.08%) | 0 (ppm) |
| (10) | 1.6% of potassium antimonyl tartrate contained (Sb: 0.6%) | 0 |
| (11) | 1.0% of bismuth oxychloride contained (Bi: 0.8%) | 0 |
| (12) | Conventional | 180–200 |

EXAMPLE 4

| Prescription (wt %) | (13) | (14) | (15) | (16) |
|---|---|---|---|---|
| Cysteine hydrochloride | 8.7 | 8.7 | 8.7 | 8.7 |
| 28% ammonia water | 3.6 | 3.6 | 3.6 | 3.6 |
| Monoethanolamine | 5.2 | 5.2 | 5.2 | 5.2 |
| Germanium dioxide | 0.06 | — | — | — |
| Potassium antimonyl tartrate | — | 0.8 | — | — |
| Bismuth oxychloride | — | — | 0.5 | — |
| EMACAL VF (above-mentioned) | 5.0 | 5.0 | 5.0 | 5.0 |
| Purified water | bal. | bal. | bal. | bal. |
| | 100 | 100 | 100 | 100 |

The pH value of these primary agents was 9.3. The concentration of each components is represented by weight percent based on all the volume of the primary agent. The results are shown in Table 4, wherein the numerical values mean ppm.

TABLE 4

| No. | Primary agents | Hydrogen sulfide produced |
|---|---|---|
| (13) | 0.06% of germanium dioxide contained (Ge: 0.04%) | 0 (ppm) |
| (14) | 0.8% of potassium antimonyl tartrate contained (Sb: 0.3%) | 0 |
| (15) | 0.5% bismuth oxychloride contained (Bi: 0.4%) | 0 |
| (16) | Conventional | 60–65 |

EXAMPLE 5

The quantities of hydrogen sulfide produced when a permanent waving operation was carried out by using a conventional primary agent for permanent waving, were detected and compared in the case that the liquid containing the deodorant according to the invention was used as a pretreatment agent for the permanent waving, and in the case of no pretreatment.

Test Method: Hair with a length of 20 cm was washed with a 0.5% aqueous solution of sodium lauryl sulfate. After washing with water thoroughly and air-drying, 3 g of hair were tied up in a bundle. The 3 g bundle of hair was wound with water around a rod with a diameter of 10 mm and air-dried. 1.2 ml of the pretreatment agent (prepared by the following prescriptions) according to the invention was applied uniformly onto the rods each by use of a 1.2 ml dropping pipette. 2.4 ml of a conventional primary agent for permanent waving was also applied uniformly onto another rod. Each of these rods was immediately charged into the sample flask (f) shown in FIG. 2 and it was closed up. The flask was settled for 15 minutes in the constant temperature chamber kept at 30° C. to continue the reaction. Hydrogen sulfide produced was determined by use of the detector tube (g) in accordance with the JIS K0108 2(3) Detector Tube Method.

| Prescription (wt %) | |
| --- | --- |
| (17) | |
| Germanium dioxide | 0.3 |
| Monoethanolamine | 0.2 |
| Sorbitol | 7.5 |
| EMACAL VF (above-mentioned) | 5.0 |
| Purified water | bal. |
| | 100 |
| (18) | |
| Potassium antimonyl tartrate | 3.0 |
| EMACAL VF (above-mentioned) | 5.0 |
| Purified water | bal. |
| | 100 |
| (19) | |
| Bismuth oxychloride | 1.4 |
| Hydrochloric acid | 1.6 |
| EDTA-2Na | 2.0 |
| 28% ammonia water | 3.4 |
| EMACAL VF (above-mentioned) | 5.0 |
| Purified water | bal. |
| | 100 |

The pH value of these pretreatment agents was about 7. The concentration of each components is represented by weight percent based on all the volume of the pretreatment agent. The results are shown in Table 5, wherein the numerical values are in the unit of ppm.

TABLE 5

| No. | Pretreatment agents | Hydrogen sulfide produced |
| --- | --- | --- |
| (17) | 0.3% of germanium dioxide contained (Ge: 0.2%) | 0 (ppm) |
| (18) | 3.0% of potassium antimonyl tartrate contained (Sb: 1.0%) | 0 |
| (19) | 1.4% of bismuth oxychloride contained (Bi: 1.1%) | 0 |
| (20) | No pretreatment | 190-200 |

Although the deodorant as the pretreatment agent in this example was used in the form of an aqueous solution, it may be used in any form, for example in the liquid-like, creamy or gelatinous form.

From the above-mentioned results, it will be understood that the primary agents for permanent waving which contain the deodorant according to the invention, i.e. a germanium, antimony or bismuth salt, and these pretreatment agents can remove hydrogen sulfide remarkably, as compared with conventional deodorants.

As far as the present invention is intended to remove the hydrogen sulfide odor resulted from a mercapto compound, it can be applied also to a hair conditioner, depilatory, shampoo, hair rinse, hair treatment agent and so on.

The test results on the stability of the primary agents for permanent waving according to the invention will be further described.

Test Example 2

Germanium dioxide, potassium antimonyl tartrate or bismuth oxychloride was added into ammonium thioglycollate in an amount of 6.0% calculated as the thioglycolic acid (TG) component, and the resulting solutions were then regulated with 28% ammonia water so that their pH value was 9.3. Thus, the primary agents for permanent waving were prepared.

The primary agents were preserved in the constant temperature chambers kept at room temperatures and at 40° C. After three months, the thioglycolic acid concentration and alkalinity of these primary agents were determined. The results are shown in Table 6.

TABLE 6

| Primary agents | Test items | Just after | After three months At room temp. | After three months At 40° C. |
| --- | --- | --- | --- | --- |
| 0.6% of germanium dioxide/contained (Ge: 0.42%) | T.G. | 6.00% | 5.90% | 5.90% |
| | Alkalinity | 5.20 ml | 5.20 ml | 5.20 ml |
| 1.2% of potassium antimonyl tartrate contained (Sb: 0.43%) | T.G. | 6.00% | 5.95% | 5.92% |
| | Alkalinity | 5.25 ml | 5.25 ml | 5.25 ml |
| 0.8% of bismuth oxychloride contained (Bi: 0.64%) | T.G. | 6.00% | 5.90% | 5.90% |
| | Alkalinity | 5.10 ml | 5.10 ml | 5.10 ml |
| Conventional | T.G. | 6.00% | 5.90% | 5.90% |
| | Alkalinity | 4.75 ml | 4.75 ml | 4.75 ml |

From the above results, it will be recognized that these primary agents seldom change even after they have been preserved in the constant temperature chambers kept at room temperatures and at 40° C. for a period of three months.

It will be understood that variations and modifications may be effected without departing from the spirit and scope of the novel concepts of this invention.

What we claim is:

1. A permanent waving preparation comprising
   (a) a mercapto compound selected from the group consisting of thioglycolic acid, cysteine, thiolactic acid, salts thereof, thioglycerol and glycerol monothioglycolate in an effective reducing amount for permanent waving, and
   (b) a salt of germanium, antimony or bismuth or mixture thereof in an amount effective to remove unpleasant odors caused by said mercapto compound, said amount being in the range of 0.01-5 weight percent as metal content.

2. A preparation as claimed in claim 1 comprising further an alkaline agent selected from the group consisting of ammonia, monoethanolamine, diethanolamine, isopronanolamine, ammonium bicarbonate, ammonium carbonate and mixture thereof, the amount of said alkaline agent being sufficient to impart to said preparation an alkaline pH effective for hair waving.

3. A permanent waving preparation as claimed in claim 2, wherein said salt of germanium, antimony or bismuth is selected from the group consisting of germanium dioxide, germanium tetrachloride, sodium metagermanate, antimony chloride, antimony sulfate, potassium antimonyl tartrate, bismuth nitrate, bismuth subnitrate, bismuth oxychloride, and mixture thereof.

4. A permanent waving preparation as claimed in claim 1, wherein said salt of germanium, antimony or bismuth is selected from the group consisting of germanium dioxide, germanium tetrachloride, sodium metagermanate, antimony chloride, antimony sulfate, potassium antimonyl tartrate, bismuth nitrate, bismuth subnitrate, bismuth oxychloride, and mixture thereof.

5. A method for alleviating unpleasant odors due to permanent waving of hair with a permanent waving preparation which includes a mercapto compound in an effective reducing amount for permanent waving, said method comprising applying to said hair, in addition to said mercapto compound, an aqueous solution containing a salt of germanium, antimony or bismuth or a mixture thereof in an amount of 0.01–5 weight percent, as metal content, based on the weight of said permanent waving preparation.

6. A method as claimed in claim 5 wherein said mercapto compound is selected from the group consisting of thioglycolic acid, cysteine, thiolactic acid, salts thereof, thioglycerol and glycerol monothioglycolate.

7. A method as claimed in claim 5, wherein said salt of germanium, antimony or bismuth is selected from the group consisting of germanium dioxide, germanium tetrachloride, sodium metagermanate, antimony chloride, antimony sulfate, potassium antimony tartrate, bismuth nitrate, bismuth subnitrate, bismuth oxychloride and mixture thereof.

8. A method as claimed in claim 5 which comprises applying to said hair a single preparation comprising said mercapto compound and said an aqueous solution containing a salt of germanium, antimony or bismuth or mixture thereof.

9. A method as claimed in claim 8 wherein said mercapto compound is selected from the group consisting of thioglycolic acid, cysteine, thiolactic acid, salts thereof, thioglycerol and glycerol monothioglycolate, and said salt or mixture thereof is present in an amount of 0.01–5 weight percent as metal content.

10. A method as claimed in claim 8 in which said preparation comprises further an alkaline agent selected from the group consisting of ammonia, monoethanolamine, diethanolamine, isopropanolamine, ammonium bicarbonate, ammonium carbonate and mixture thereof, the amount of said alkaline agent being sufficient to impart to said preparation an alkaline pH effective for hair waving.

11. A method as claimed in claim 5 in which said hair is pretreated with an aqueous solution containing said salt of germanium, antimony, bismuth or mixture thereof, and is then treated with said mercapto compound.

12. A method as claimed in claim 11 wherein said aqueous solution comprises further an alkaline agent selected from the group consisting of ammonia, monoethanolamine, diethanolamine, isopropanolamine, ammonium bicarbonate, ammonium carbonate and mixture thereof, the amount of said alkaline agent being sufficient to impart to said aqueous solution an alkaline pH effective for hair waving.

* * * * *